US008084632B2

(12) United States Patent
Liu et al.

(10) Patent No.: US 8,084,632 B2
(45) Date of Patent: Dec. 27, 2011

(54) METHODS FOR ENHANCING THE EFFICIENCY OF RHENIUM-PROMOTED EPOXIDATION CATALYSTS AND EPOXIDATION METHODS UTILIZING THESE

(75) Inventors: Albert C. Liu, Charleston, WV (US); Liping Zhang, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 12/754,200

(22) Filed: Apr. 5, 2010

(65) Prior Publication Data

US 2010/0267973 A1      Oct. 21, 2010

Related U.S. Application Data

(60) Provisional application No. 61/171,207, filed on Apr. 21, 2009.

(51) Int. Cl.
  *C07D 301/03*   (2006.01)
  *C07C 209/00*   (2006.01)
  *C07C 31/18*    (2006.01)
  *C07C 27/00*    (2006.01)
  *C07C 41/00*    (2006.01)
(52) U.S. Cl. ........ 549/523; 564/487; 568/852; 568/867; 568/579

(58) Field of Classification Search .................. 549/536, 549/523; 564/487; 568/579, 852, 867
See application file for complete search history.

(56) References Cited

U.S. PATENT DOCUMENTS

| | | | |
|---|---|---|---|
| 4,766,105 A | 8/1988 | Lauritzen |
| 4,822,900 A | 4/1989 | Hayden |
| 5,187,140 A | 2/1993 | Thorsteinson et al. |
| 5,504,053 A | 4/1996 | Chou et al. |
| 2009/0082584 A1 | 3/2009 | Rizkalla et al. |

FOREIGN PATENT DOCUMENTS

| | | |
|---|---|---|
| EP | 0 352 850 A1 | 1/1990 |
| WO | 2004002954 A2 | 1/2004 |
| WO | 2004002972 A2 | 1/2004 |

OTHER PUBLICATIONS

International Search Report and Written Opinion for PCT/US2010/029948, Aug. 25, 2010.

*Primary Examiner* — Taylor Victor Oh (74) *Attorney, Agent, or Firm* — Lois K. Ruszala; KSJLaw, LLC (57) ABSTRACT

A method for enhancing the efficiency of a rhenium-promoted epoxidation catalyst is provided. Advantageously, the method may be carried out in situ, i.e., within the epoxidation process, and in fact, may be carried out during production of the desired epoxide. As such, a method for the epoxidation of alkylenes incorporating the efficiency-enhancing method is also provided, as is a method for using the alkylene oxides so produced for the production of 1,2-diols, 1,2-carbonates, 1,2-diol ethers, or alkanolamines.

18 Claims, 4 Drawing Sheets

Example of catalyst activation

Figure 1. Example of catalyst activation

Figure 2. Example of catalyst activation

METHODS FOR ENHANCING THE EFFICIENCY OF RHENIUM-PROMOTED EPOXIDATION CATALYSTS AND EPOXIDATION METHODS UTILIZING THESE

FIELD OF THE INVENTION

Provided herein are methods for enhancing the efficiency of epoxidation catalysts. Advantageously, the method is capable of being incorporated into an epoxidation method, so that production can continue during the efficiency enhancement and so, epoxidation methods utilizing the enhanced catalysts are also provided.

BACKGROUND

Catalysts are important components of many chemical manufacturing processes, and may typically be used to accelerate the rate of the reaction in question and/or to increase the selectivity or efficiency towards the desired product(s). Utilized in connection with many reactions, catalysts find particular advantageous use in the epoxidation of olefins, a process of significant commercial importance in the commodity chemical business. In epoxidation reactions, a feed containing at least the olefin and oxygen is contacted with a catalyst causing the formation of the corresponding olefin oxide.

One example of an olefin epoxidation of particular commercial importance is the epoxidation of alkylenes, or mixtures of alkylenes, and this epoxidation reaction in particular can rely upon high performing catalysts in order to be commercially viable. Typically, catalysts used in alkylene epoxidation comprise a catalytic species deposited on a suitable support/carrier alone or in combination with one or more promoters.

Those of skill in the art have actively sought improvements in the efficiency and/or activity of epoxidation catalysts for some time, since, on a commercial scale, even slight, e.g., 1%, increases in selectivity can reduce the operating costs associated with the epoxidation processes, substantially.

Research in this area has been wide ranging, and improvements that may provide the catalysts with increased efficiency and/or an extended useful life have been sought in the areas of components of the catalyst, e.g., carriers, promoters, and catalytic species, methods of making the catalyst and even the epoxidation processes themselves. However, it is often the case that adjustments in one or more of these may result in an improvement in one of catalyst efficiency, activity, or lifetime while yet resulting in a concurrent decrement in another. Or, any such adjustments may require conditions that cannot be produced within the epoxidation process, or if reproducible therewithin, require a reduction, or complete shut-down, in the production of the epoxidation product.

Desirably, methods would be provided that could be utilized to enhance the efficiency and/or activity of such epoxidation catalysts. Any such methods would be particularly beneficial if they could provide such enhancements over the lifetime of the catalyst, and in particular, if they could be utilized in situ, i.e., while the catalyst is in place, and/or being used in an epoxidation reaction.

SUMMARY OF THE INVENTION

The present invention provides methods for enhancing the efficiency of epoxidation catalysts. The enhancements to efficiency reduce raw material consumption and waste production. The efficiency enhancements may also, in turn, result in the catalysts being capable of providing commercially acceptable through-puts for a greater length of time, so that the typically expensive and time-consuming catalyst change-out may be required less frequently. Advantageously, the present methods may be carried out within epoxidation equipment, thereby providing time savings in these embodiments of the invention. Additionally, the present method may be carried out during start-up, or at any point during the epoxidation process without a substantial decrease in through-put, so that additional cost-savings may be provided in certain embodiments.

In a first aspect, the present invention provides a method for enhancing the efficiency of a rhenium-promoted epoxidation catalyst. The method comprises contacting the catalyst with a feed comprising a gas phase epoxidation reaction promoter at an elevated temperature of at least about 240° C., or, in some embodiments of less than or equal to 250° C., for at least about 2 hours, or for at least about 6 hours, preferably for at least about 12 hours, or even for at least about 24 hours, or longer. The temperature is then reduced to a temperature of less than or equal to about 230° C. Advantageously, the gas-phase promoter concentration can be maintained during the period at elevated temperature, or if desired, the promoter concentration can be caused to differ. Application of the present method to epoxidation catalysts may result in increases in the efficiency of the catalyst of at least about 0.1%, or even at least about 1.0%, relative to the efficiency of the catalyst prior to initiation of the method.

Advantageously, the method of the present invention may be carried out in situ, i.e., within epoxidation equipment during start-up or normal operation of the epoxidation process. Because the method may provide the catalysts with an enhanced lifetime, the time period between catalyst change-outs may be lengthened and cost and time savings may be realized.

In a second aspect then, the present invention provides a method for the epoxidation of one or more alkylenes. The method comprises contacting the catalyst with a feed comprising a gas phase epoxidation reaction promoter, oxygen and one or more alkylenes at an elevated temperature of at least about 240° C. for at least about 2 hours, or for at least about 6 hours, or at least about 12 hours, or even at least about 24 hours, or longer. The temperature is subsequently reduced to a temperature of less than or equal to about 230° C. Advantageously, the concentration of the promoter, oxygen and one or more alkylenes may remain constant, or if desired, may be altered during one or more of the temperature stages.

DESCRIPTION OF THE DRAWINGS

These and other features, aspects and advantages of the present invention may be further understood and/or illustrated when the following detailed description is considered along with the attached drawings.

DETAILED DESCRIPTION OF THE INVENTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof; rather, and unless otherwise noted, terms are to be understood according to conventional usage by those of ordinary skill in the relevant art.

Unless defined otherwise, technical and scientific terms used herein have the same meaning as is commonly understood by one of skill in the art to which this invention belongs. The "selectivity" of an epoxidation reaction, which is synonymous with "efficiency," refers to the fraction, expressed as a percentage, of converted or reacted olefin that forms the corresponding olefin oxide product. The terms "efficiency" and "selectivity" are used interchangeably herein. The activity of an epoxidation reaction can be quantified in a number of ways, one being the mole percent of olefin oxide contained in an outlet stream of the reactor relative to that in an inlet stream (the mole percent of olefin oxide in the inlet stream typically, but not necessarily, approaches zero percent) while the reactor temperature is maintained substantially constant; and another being the temperature required to maintain a given rate of olefin oxide production. In many instances, activity is measured over a period of time in terms of the mole percent of olefin oxide produced at a specified constant temperature. Alternatively, activity can be measured as a function of the temperature required to sustain production of a specified constant mole percent of olefin oxide.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

The present invention provides a method to enhance the efficiency of a rhenium-promoted epoxidation catalyst. More particularly, the method comprises contacting the catalyst with a feed comprising a gas phase epoxidation reaction promoter at a temperature of at least about 240° C. for at least about 2 hours, or at least about 6 hours, or at least about 12 hours, or even at least about 24 hours or longer, and then reducing the temperature to a temperature of less than or equal to about 230° C.

Advantageously, the method of the present invention can be carried out in the presence of a feed stream having a composition typical for epoxidation processes. For example, the feed stream may comprise, and the method of the present invention may be carried out in the presence of, one or more gas phase epoxidation reaction promoters.

Gas phase epoxidation reaction promoters are thought to be capable of increasing the efficiency and/or activity of epoxidation catalysts by either increasing the rate towards the formation of the desired alkylene oxide and/or suppressing the oxidation of alkylene or alkylene oxide to form carbon dioxide and water, relative to the formation of the desired alkylene oxide. Many such promoters are known, and any of these may be used in the method of the present invention. Typically, gas phase promoters useful in epoxidation reactions include organic compounds, and in particular include organic halides, e.g., bromides or chlorides. "Promoters" are sometimes referred to as "inhibitors", "modifiers", "enhancers" or "moderators"

Of these, chlorohydrocarbons are particularly preferred. Suitable gaseous chlorohydrocarbons include those having from one to eight carbon eights. Examples of these include, but are not limited to, methyl chloride, ethyl chloride, ethylene dichloride, vinyl chloride, or any combination of these. Particularly preferred gas phase epoxidation reaction promoters for use in the present method are ethyl chloride and ethylene dichloride.

Using chlorohydrocarbon gas phase promoters as an example, it is believed that the ability of the promoter to enhance the performance (e.g., efficiency and/or activity) of the process for the desired alkylene oxide depends on the extent to which the gas phase promoter chlorinates the surface of the catalyst, for example, by depositing a particular chlorine species such as atomic chlorine or chloride ions on the catalyst. However, hydrocarbons lacking chlorine atoms are believed to strip chlorides from the catalyst, and therefore, detract from the overall enhancement provided by the gas phase promoter. Discussions of this phenomenon may be found in Berty, "Inhibitor Action of Chlorinated Hydrocarbons in the Oxidation of Ethylene to Ethylene Oxide," Chemical Engineering Communications, Vol. 82 (1989) at 229-232 and Berty, "Ethylene Oxide Synthesis," Applied Industrial Catalysis, Vol. I (1983) at 207-238. Paraffinic compounds, such as ethane or propane, are believed to be especially effective at stripping chlorides from the catalyst. However, olefins, such as ethylene and propylene, are also believed to act to strip chlorides from the catalyst. Some of these hydrocarbons may also be introduced as impurities in the ethylene feed or may be present for other reasons (such as the use of a recycle stream). Typically, the preferred concentration of ethane in the feed, when present, is from 0 to about 2 mole percent.

Given the competing effects of the gas phase promoter and the non-halogenated, non-promoting hydrocarbons in the reactor feed stream, it is convenient to define an "overall halogenating effectiveness value," which in the case of organic chlorides is an "overall chloriding effectiveness value" that represents the net effect of the promoting and non-promoting gas phase species in halogenating (or chloriding) the catalyst. In the case of organic chloride gas-phase promoters, the overall chloriding effectiveness can be defined as the dimensionless quantity $Z^*$ and represented by the following formula I:

$$Z^* = \frac{\text{ethyl chloride equivalent } (ppmv)}{\text{ethane equivalent (mole percent)}} \quad \text{(I)}$$

wherein the ethyl chloride equivalent is the concentration in ppmv of ethyl chloride that provides substantially the same catalyst chloriding effectiveness of the organic chlorides present in the reactor feed stream at the concentrations of the organic chlorides in the feed stream; and the ethane equivalent is the concentration of ethane in mole percent that provides substantially the same catalyst dechloriding effectiveness of the non-chloride containing hydrocarbons in the feed stream at the concentrations of the non-chloride containing hydrocarbons in the feed stream.

If ethyl chloride is the only gaseous chloride-containing promoter present in the reactor feed stream, the ethyl chloride equivalent is the ethyl chloride concentration in ppmv. If another chlorine-containing promoter (specifically vinyl chloride, methyl chloride or ethylene dichloride) is used alone or in conjunction with ethyl chloride, the ethyl chloride equivalent is the sum of the concentration of ethyl chloride in ppmv and the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride.

As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed having of 1 ppmv ethylene dichloride and 1 ppmv ethyl chloride, the ethyl chloride equivalent in the numerator of $Z^*$ would then be 3 ppmv. As a further example, it has been found for certain catalysts that methyl chloride has 10 times less the chloriding effectiveness of ethyl chloride. Therefore, for such catalysts, the ethyl chloride equivalent for a given concentration of methyl chloride in ppmv is 0.1×(methyl chloride concentration in ppmv).

The ethane equivalent is the concentration of ethane in mole percent in the reactor feed stream plus the concentrations of the other hydrocarbons effective in removing chloride from the catalysts, corrected for their effectiveness for dechlorination relative to ethane. The relative effectiveness of ethylene and ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane.

As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed having 30.0 mole percent ethylene and 0.3 mole percent ethane, the ethane equivalent will then be 0.6 mole percent.

As another illustration, it has been found that, for certain catalysts, methane has 500 times less the dechloriding effectiveness of ethane. Thus, for such catalysts, the ethane equivalent for methane is 0.002×(methane concentration in mole %). For a typical inlet reactor feed having 30.0 mole percent ethylene and 0.1 mole percent ethane, the ethane equivalent then will be 0.4 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its feed concentration at two different feed ethane concentrations. If a hydrocarbon compound is found to have a very small dechloriding effect and is also present in low concentrations, then its contribution to the ethane equivalent concentration in the $Z^*$ calculation will be negligible.

Thus, given the foregoing relationships, in the case where the reactor feed stream includes ethylene, ethyl chloride, ethylene dichloride, vinyl chloride, and ethane, the overall chloriding effectiveness value of the process can be defined by the following formula (II):

$$Z^* = \frac{(ECL + 2*EDC + VCL)}{(C_2H_6 + 0.01*C_2H_4)} \quad \text{(II)}$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in the reactor feed stream. $C_2H_6$ and $C_2H_4$ are the concentrations in mole percent of ethane and ethylene, respectively, in the reactor feed stream.

In those embodiments of the invention wherein the method is applied during/within an epoxidation process, those of skill in the art will recognize that although a single chlorohydrocarbon gas phase promoter may be utilized in some embodiments of the invention, upon contact with the catalyst under epoxidation reaction conditions, a variety of compounds may be formed and thus are present whether or not a recycle loop is utilized in the process. As such, it is to be understood, that even if one, or a certain, gas phase promoter is initially utilized in the present method, the scope of the claims is considered to include not only the introduced promoter(s), but any or all of its/their reaction products that may be formed during application of the method.

The concentration of the gas phase epoxidation reaction promoter can remain substantially the same, or can be altered, during the method. Advantageously, and due to the at times undesired effects of increasing the overall catalyst chloriding effectiveness value on the activity of certain epoxidation catalysts, in certain embodiments of the invention, the overall catalyst chloriding effectiveness value is maintained at a substantially constant level during at least the treatment at temperatures of at least 240° C. In other embodiments of the invention, the overall catalyst chloriding effectiveness value may even be decreased during treatment at temperatures of 240° C. or higher, or less than or equal to 250° C.

The method of the present invention makes use of a period of operation at an elevated temperature to enhance the efficiency of the epoxidation catalyst, during start-up or use of the catalyst in an epoxidation process. As used herein, the phrase "elevated temperature" means a temperature elevated relative to the reduced temperature, e.g., of less than or equal to about 230° C. Desirably, the elevated temperature is at least about 240° C., or as high as 250° C., or even higher. Maintaining the elevated temperature of at least 240° C. for even short periods of time, e.g., at least about 2 hours, or at least about 6 hours, at least about 12 hours, or even at least about 24 hours, or longer has now been found to be capable of providing significant increases in efficiency, e.g., at least about 0.1%, or at least about 0.5%, or even at least about 1%, relative to the efficiency of the catalyst prior to initiation of the method.

It is to be understood that such increases may or may not be substantially cumulative. However, even in those embodiments of the invention wherein one or more periods at an elevated temperature may be employed, and may exhibit cumulative effects on the efficiency of the catalyst, it is to be understood that the capability of the invention to provide the results described herein will be limited at least by the theoretical maximum efficiency of the catalyst. The theoretical maximum efficiency for any given catalyst refers to the maximum efficiency at close to zero alkylene or oxygen conversion, or close to zero alkylene oxide concentration under the most favorable, practical, temperature, pressure, gas hourly space velocity and feed composition (including optimized gas phase promoter levels). It can be obtained, for example, by obtaining efficiency versus alkylene oxide concentration curves under the best known reaction conditions for the given catalyst by varying the reaction temperature and then extrapolating the curve to zero alkylene oxide concentration. The extrapolated efficiency at zero alkylene oxide concentration can be considered as the theoretically maximum efficiency for the given catalyst.

The elevated temperature will desirably be maintained for long enough to provide at least a minimal increase in efficiency of the catalyst relative to the efficiency of the catalyst prior to initiation of the present method, e.g., at least about 0.1%, once the temperature is reduced. The elevated temperature may desirably be maintained, e.g., for at least about 2 hours, or even about 6 hours, or 12 hours, or 24 hours, or 48 hours, or 72 hours, or for five days, or even 1 week. Especially in those embodiments of the invention where the method is carried out in situ, it may be advantageous to utilize the most expedient efficiency enhancing embodiment, and maintaining the elevated temperature for about 2 to about 24 hours can be preferred.

After the desired time at the elevated temperature, the temperature will desirably be reduced. The temperature may reduced by any desired amount relative to the elevated temperature. In some embodiments, the temperature may be reduced to the desired operating temperature of the process. As is known to those of skill in the art, the desired operating temperature for an epoxidation process may typically vary, e.g., over the life of the catalyst. In certain preferred embodiments, the temperature will be reduced to 230° C. or less, after the desired period at the elevated temperature.

The changes in temperature can be caused to occur in one or multiple steps, and may be caused manually or by a control system. It is further to be understood that either or both of temperature elevation or reduction may take place as smooth functions, or as stepwise functions. Because of this, as well as standard fluctuations provided by commercial temperature controllers, the particular temperatures discussed herein include at least the standard deviation associated with the measuring equipment and/or the temperature controller(s).

The temperature values in this invention refer to the gas phase temperatures in the catalyst bed. As those of ordinary skill in the chemical processing art are aware, temperatures of manufacturing processes may typically be measured directly or indirectly.

Direct measurements of the temperature of the catalyst bed may be obtained, e.g., by operatively disposing a thermocouple or a fiber optic probe relative to the catalyst bed. Multiple thermocouples or fiber optic probes may be utilized, in which case, a weighted average based on thermocouple/probe position and spacing in the bed can be used to represent the temperature. Alternatively, an average temperature may be obtained via mathematical integration of the measured temperature profile along the catalyst bed.

The catalyst bed temperature may be also indirectly measured and/or calculated, e.g., via combining the measurement and/or calculation of coolant temperatures and reaction heat generation, measurement of reactor effluent stream temperature, simulation methods that combine a priori knowledge about the system (plant data) with a mathematical model to provide a real-time estimation of the temperature profile along the catalyst bed, etc. For reactors using boiling water as coolant, the coolant temperature can also be accurately calculated based on the measured steam pressure in the reactor shell.

Because of the ease of use associated therewith, many commercial epoxidation production facilities utilize indirect measurements and/or calculations, and these can be used in the present method, with measurement of outlet gas temperatures being preferred. It is to be understood that the measurement technique utilized is not critical, so long as the elevated temperature used is at least about 240° C., and the reduced temperature is less than or equal to about 230° C. inclusive of at least the standard deviation associated with the measurement apparatus and any expected temperature difference between an indirect and direct measurement, should an indirect measurement method be employed. For example, it is known, due to the exothermic nature of epoxidation reactions, that the average catalyst bed temperature is higher than the coolant temperature. The exact difference depends on reactor design, operating conditions, and catalyst performance. For example, for an ethylene epoxidation system with high efficiency catalyst (e.g., $\geqq 85\%$) and with boiling water as the coolant, the average temperature in the catalyst bed is typically within about 10° C. higher than the coolant temperature.

As those of ordinary skill in the chemical engineering art are aware, there are many suitable ways for adjusting the reaction temperature within a chemical process, including, but not limited to, temperature, flow rate, and pressure of the coolant; reactor feed composition, space velocity, and pressure, etc., and any of these may be utilized to adjust the temperature of the present process.

The present method can be utilized to enhance the efficiency of an epoxidation catalyst during start-up or use, or it may be utilized to re-activate catalysts that have been used, but due to planned or unplanned shut-down, have been subjected to a period of inactivity. In other words, and surprisingly, the present method can be effective to provide increases of efficiency of at least about 0.1% to catalysts that have been, or are being, exposed to feed gas comprising the desired reactant, e.g., one or more olefins, relative to the efficiency of the catalyst prior to initiation of the method.

One class of catalysts that may find particular benefit from application of the present invention includes those useful for the epoxidation of olefins, and in particular, for the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, 4$^{th}$ Ed. (1994) Volume 9, pages 915-959, all of which are incorporated by reference herein in their entirety for any and all purposes. Although the invention is not so limited, for purposes of simplicity and illustration, application of the present method is further described in terms of and with reference to catalysts useful for the epoxidation of ethylene.

Generally, such catalysts are supported catalysts, and may comprise any of the large number of known porous refractory structure or support materials, so long as whatever the porous refractory material chosen, it is relatively inert in the presence of the chemicals and processing conditions employed in the application in which the shaped porous body will be utilized. It may also be important that the support materials, and thus catalysts based upon the same, be able to withstand fairly large temperature and pressure fluctuations within the reactor.

There are many well-known methods of preparing supports suitable for use in alkylene oxide catalysts. Some of such methods are described in, for example, U.S. Pat. Nos. 4,379,134; 4,806,518; 5,063,195; 5,384,302; 6,831,037 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, and their degree of volatilization during the calcination step. Common impurities may include silica, alkali and alkaline earth metal oxides and trace amounts of metal and/or non-metal-containing additives. Another method for preparing a support having particularly suitable properties for alkylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina support.

In one embodiment, the support material comprises at least about 80 weight percent alpha-alumina and comprises less than about 30 parts per million acid-leachable alkali metals by weight, the weight percent of the alpha-alumina and the concentration of the acid-leachable alkali metals being calculated on the weight of the support, where the acid-leachable alkali metals are selected from lithium, sodium, potassium, and mixtures thereof.

Preparation of the support material may further comprise any other component, in any amounts, necessary or desired for processing, such as, e.g., water, acid, binders, lubricants, dispersants, pore formers, dopants, modifiers, etc, such as those described in *Introduction to the Principles of Ceramic Processing*, J. Reed, Wiley Interscience, (1988), incorporated herein by reference.

The support material(s) will desirably be porous and have measured surface areas of at least about 0.5 m$^2$/g (more preferably from about 0.7 m$^2$/g to about 10 m$^2$/g), measured pore volumes of at least about 0.3 cc/g (more preferably from about 0.4 cc/g to about 2.0 cc/g), and median pore diameters from about 1 to about 50 microns.

"Surface area", as used herein, refers to the surface area as measured by the BET (Brunauer, Emmett and Teller) method by nitrogen as described in the Journal of the American Chemical Society 60 (1938) pp. 309-316. "Total pore volume" means pore volume of the support material and is typically determined by mercury porosimetry. "Porosity" is the proportion of the non-solid volume to the total volume of material. Total pore volume as measured by mercury porosimetry or water absorption may be used to estimate porosity by those of skill in the art. "Median pore diameter" means the pore diameter corresponding to the point in the pore size distribution at which half of the total pore volume of the shaped porous body has been measured.

The support materials/catalysts can be of any desired, suitable shape. Conventional commercial fixed bed ethylene oxide reactors are typically in the form of a plurality of parallel elongated tubes (in a suitable shell) having an outer diameter of from about 2 to 7 cm and a length of from about 4 to 14 m. For use in such fixed bed reactors, the support materials/catalysts will desirably be formed into a rounded shape, such as, for example, spheres, pellets, rings, tablets, and the like, having diameters from about 0.1 inch (0.25 cm) to about 0.8 inch (2 cm).

In addition to the support material, epoxidation catalysts include at least one catalytic species deposited thereupon. Non-limiting examples of catalytic species that may advantageously be supported by the support material include metals, solid state compounds, molecular catalysts, enzymes and combinations of these. Typically, catalysts useful for the epoxidation of ethylene utilize silver as the catalytic species, and the same is preferred in these embodiments of the invention.

Some conventional methods for the initialization or improvement of efficiency of epoxidation catalysts require limitation of the amount of silver utilized in the catalyst. More particularly, and because some methods of improving catalyst efficiency require temperatures of greater than 250° C., and/or introduction of reactive gases, e.g., oxygen, that can result in contact sintering of silver, these methods can require the utilization of reduced concentrations, or densities, of silver relative to the support material.

Advantageously, the present method does not suffer from these limitations, and any desired catalytic amount of silver, i.e., any amount of silver capable of catalyzing the direct oxidation of, e.g., ethylene, with oxygen or an oxygen-containing gas to the corresponding alkylene oxide, may be used. Typically, the support material will be impregnated one or more times with silver compound solutions sufficient to allow the silver to be provided on the support material in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Although the amount of silver utilized is not particularly limited, the amount of silver provided in connection with the support material may usually be less than about 70 percent, and more preferably, less than about 50 percent by weight, based on the weight of the catalysts.

In terms of density, the catalytic species, e.g., silver, relative to the surface area of the support material may be present in amounts up to at least about 0.07 g/m$^2$, or up to about 0.2 g/m$^2$, or even up to about 0.3 g/m$^2$ or more.

Although silver particle size in the finished catalysts is important, the range is not narrow. A suitable silver particle size can be in the range of from about 10 angstroms to about 10,000 angstroms in diameter. A preferred silver particle size ranges from greater than about 100 angstroms to less than about 5,000 angstroms in diameter. It is desirable that the silver be relatively uniformly dispersed within, throughout, and/or on the shaped porous body.

Catalysts according to the present invention desirably comprise rhenium, and may, in certain embodiments, further include one or more additional promoters. Rhenium promoted supported silver containing catalysts are known from U.S. Pat. No. 4,761,394 and U.S. Pat. No. 4,766,105, which are incorporated herein by reference. Broadly, the catalysts comprise silver, rhenium or compound thereof, and in some embodiments, a co-promoter such as a further metal or compound thereof and optionally an additional co-promoter such as one or more of sulfur, phosphorus, boron, and compounds thereof, on the support material. As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

Known promoters for silver based catalysts for the epoxidation of ethylene include, but are not limited to, rhenium, molybdenum, tungsten, lithium, sulfur, manganese, potassium, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference in their entirety for any and all purposes.

The rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Catalysts comprising silver as a catalytic species as well as at least rhenium as a promoter are expected to find particular benefit from application of the present invention, and such catalysts are preferred. In some embodiments, the catalysts may also desirably comprise a promoting amount of at least one further metal, and optionally, a co-promoter. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, sodium, rubidium and cesium and/or from the Group IIA metals such as calcium, strontium, and barium. Most preferably it is lithium, potassium, sodium and/or cesium. The metals, as well as the rhenium promoter may each be present in a quantity of from 0.01 to 500 mmole/kg, calculated as the element (rhenium or metal) on the total catalyst. Optional co-promoters include, but are not limited to: tungsten, manganese, molybdenum, chromium, sulfur, phosphorous, boron, and mixtures thereof.

The supported silver catalyst can comprise a rhenium promoter, a first co-promoter, and a second co-promoter; where the quantity of the rhenium promoter deposited on the carrier is greater than 1 mmole/kg, relative to the weight of the catalyst; where the first co-promoter is selected from sulfur, phosphorus, boron, and mixtures thereof; where the second co-promoter is selected from tungsten, molybdenum, chromium, and mixtures thereof; and the total quantity of the first co-promoter and the second co-promoter deposited on the carrier is at most 3.8 mmole/kg, relative to the weight of the catalyst.

The catalyst can comprise a carrier and, deposited on the carrier, silver, a rhenium promoter, a first co-promoter, and a second co-promoter; wherein the molar ratio of the first co-promoter to the second co-promoter is greater than 1, wherein the first co-promoter is selected from sulfur, phosphorus, boron, and mixtures thereof; and wherein the second co-promoter is selected from tungsten, molybdenum, chromium, and mixtures thereof. The catalyst can comprise silver, a rhenium promoter, a first co-promoter, and a second co-promoter on a carrier; wherein the molar ratio of the first co-promoter to the second co-promoter is greater than 1; wherein the first co-promoter is selected from sulfur, phosphorus, boron, and mixtures thereof; and the second co-promoter is selected from tungsten, molybdenum, chromium, and mixtures thereof.

The rhenium and any other desired promoters included in the catalyst to be subjected to the present method are desirably provided in a promoting amount, and such amounts are readily determined by those of ordinary skill in the art. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Exemplary suitable amounts of rhenium are expected to range from about 0.0001 weight percent (1 ppmw) to 2 weight percent (20,000 ppmw), preferably from about 0.0005 weight percent (5 ppmw) to 0.5 weight percent (5000 ppmw) based on the total weight of the catalyst. When used, the rhenium component may often be provided in an amount of at least about 1 ppmw, say, at least about 5 ppmw, for example, or from about 10 ppmw to about 2000 ppmw, often between about 20 ppmw and 1000 ppmw, calculated as the weight of rhenium based on the total weight of the catalyst.

Methods of preparing epoxidation catalysts are well-known in the art, and any of these are suitable for use in preparing the catalysts to be subjected to the present methods. Generally speaking, the methods involve one or more impregnation steps with one or more solutions comprising the desired catalyst components. Typically, a reduction step is conducted during or after the impregnations, to form metallic silver particles. Thorsteinson et al., U.S. Pat. No. 5,187,140, for example, describes methods of forming catalysts, and is incorporated herein by reference for any and all purposes.

It has now been surprisingly discovered that epoxidation catalysts can be re-activated, or have the efficiency thereof enhanced, by subjecting the catalysts to an elevated temperature in the presence of a gas phase epoxidation reaction promoter. Advantageously, the method of the present invention can be utilized in situ, that is, when the catalyst is in place in epoxidation processing equipment during start-up or operation of the process, without substantial fluctuation in the production of the desired alkylene oxide. Application of the present method can provide increased time intervals between catalyst change-out, and thus, provides significant cost and time savings. Further cost savings can be realized in the form of raw material savings provided by the increased catalyst efficiency after application of the method. The present method can also result in decreased production of the by-product carbon dioxide, and so, the present method also provides environmental benefits.

As such, the present invention also provides a method for the epoxidation of alkylenes. Those of ordinary skill in the chemical engineering art are familiar with such processes. One exemplary process is described in Kirk-Othmer's Encyclopedia of Chemical Technology, $4^{th}$ ed., Vol. 9, 1994, pp. 925-939, and the contents of this article are hereby incorporated herein by reference for any and all purposes.

Generally speaking then, the epoxidation reaction may take place in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics.

The epoxidation reaction is generally exothermic. Thus, a coolant system (e.g., a cooling jacket or a hydraulic circuit with a coolant fluid such as a heat transfer fluid or boiling water) may be provided to regulate the temperature of the reactors. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature.

Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas and a gas phase promoter at parts per million level to a catalyst-containing reactor at a temperature of from about 200° C. to about 300° C., and a pressure which may vary between about 5 atmospheres (506 kPa) and about 30 atmospheres (3.0 MPa), depending upon the mass velocity and productivity desired. Oxygen may be supplied to the reaction in an oxygen-containing stream, such as air, or as pure oxygen, or as oxygen-enriched air. The resulting alkylene oxide, preferably, ethylene oxide, is separated and recovered from the reaction products using conventional methods.

Any alkylene can be utilized in the process, and examples of those that may desirably be epoxidized include, but are not limited to, 1,9-decadiene, 1,3-butadiene, 2-butene, isobutene, 1-butene, propylene, ethylene, or combinations of these. Preferably, the alkylene comprises ethylene.

Typically, epoxidation reactions may desirably be carried out in the gas phase, with a feed comprising the desired alkylene and oxygen being caused to come in contact with an epoxidation catalyst. Oftentimes, the catalyst is present as a solid material, and more particularly, may be present as a packed bed within the desired reactor. The quantity of catalyst in the packed bed may be at least about 10 kg, or at least 20 kg, or from about $10^2$ to $10^7$ kg or from about $10^3$ to $10^6$ kg.

Many epoxidation reactions are carried out as continuous processes, and the same is contemplated here. In such processes, the desired reactor may typically be equipped with heat exchange equipment to control the temperature of the process, within the reactor and/or the catalyst bed.

The feed may additionally comprise one or more optional components, including, for example, carbon dioxide, inert gases, saturated hydrocarbons and the like. Carbon dioxide may, in particular, be expected to be present when recycling of the feed is conducted, since carbon dioxide is a by-product of many epoxidation processes. In these embodiments, at least part of the carbon dioxide in the recycled gas is removed via conventional ways such as those described in Kirk-Othmer's Encyclopedia of Chemical Technology, $4^{th}$ Ed. (1994) Volume 9, pages 915-959, since carbon dioxide has an adverse effect on catalyst performance, especially activity. The inert gas may comprise nitrogen, argon, or mixtures thereof. Saturated hydrocarbons such as methane may be utilized to control heat within the reactor and allow a higher oxygen concentration in the feed.

In one embodiment, the process for the oxidation of an alkylene comprises contacting a reaction mixture feed comprising an alkene, oxygen, and carbon dioxide, with a catalyst comprising a carrier and, deposited on the carrier, silver, a rhenium promoter, a first co-promoter, and a second co-promoter; wherein the carbon dioxide is present in the reactor mixture in a quantity of at most 3 mole percent based on the total reaction mixture; the first co-promoter is selected from sulfur, phosphorus, boron, and mixtures thereof; and the second co-promoter is selected from tungsten, molybdenum, chromium, and mixtures thereof.

During operation, the pressure at the inlet of the epoxidation reactor may typically be less than 4000 kPa, or less than 3500 kPa, or preferably will be less than about 2500 kPa absolute, and in most instances will be at least 1000 kPa absolute. The gas hourly space velocity, ("GHSV") is the unit volume of gas at standard state temperature and pressure (0° C., 1 atm) passing over one unit volume of packed catalyst bed per hour. Preferably in those embodiments wherein the epoxidation reaction is carried out in the gas phase, over a packed catalyst bed, the GHSV in the start-up phase is desirably from about 2000 to about 10000 per hour.

One particular example of an epoxidation process wherein the method of the present invention is applied during operation may proceed as follows. At any time during start-up or operation, when the temperature is below about 250° C., preferably below about 240° C., and catalyst efficiency may desirably be enhanced, the operating temperature will be increased to at least about 240° C. and up to about 250° C. for a period of at least about 2 hours, at least about 6 hours, at least about 12 hours, at least about 24 hours, about 48 hours, about 72 hours, or for five days, or even 1 week. After the desired time period, the temperature is reduced, e.g., to 230° C. or below, and preferably to a temperature corresponding to a desired production rate of alkylene oxide.

During periods at elevated temperatures of 240° C. or above, the feed composition may remain substantially unchanged. More particularly, during periods of elevated temperature, the reactor inlet oxygen concentration may desirably remain substantially unchanged, e.g., at about 8 mole-%, the reactor inlet alkylene concentration may desirably remain substantially unchanged, e.g., at about 30 mole-%, the inlet carbon dioxide concentration may also remain substantially unchanged, e.g., at about 3 mole-% and the overall catalyst chloriding effectiveness value may remain substantially unchanged, e.g., at about 3 when expressed as $Z^*$.

Alternatively, the feed composition may be altered during the periods at elevated temperatures of 240° C. or above in order to maintain desired levels of alkylene oxide production during application of the present method. More particularly, when the method is employed with a catalyst that is already in use, concurrent with the periods at elevated temperature, the reactor inlet oxygen concentration may be decreased, e.g., by at least about 1 mole-%, or by about 2 mole-% or even about 3 mole-%, so long as safe operating conditions and desired alkylene oxide production are maintained. The inlet carbon dioxide concentration may advantageously be increased, e.g., by at least about 0.5 mole-%, or about 1 mole-%, the amount of such increase in certain cases being limited by the design of the epoxidation process. The overall catalyst chloriding effectiveness value may advantageously be decreased, e.g., by at least about 0.5 or even 1.0 or more $Z^*$ units, the amount of such decrease being limited in certain cases by the amount of recycle in the process design. The inlet alkylene concentration may be substantially maintained, or, may be decreased by about 5 or 10 or even 15 mole-%, concurrent with the period (s) at elevated temperature. In some embodiments of the invention, the inlet concentration of just one of the feed components is adjusted in correspondence with the period at elevated temperature. In other embodiments, particular combinations of two or more of the feed components may be varied in order to substantially maintain a desired level of alkylene oxide production at elevated temperature. In any case, whenever such adjustments in the composition of the feed gas are made concurrently with operation at elevated temperature, it can be preferred to return the adjusted concentrations to substantially their prior levels when subsequently operating at reduced temperature, or to other combinations of concentrations that advantageously provide the desired level of alkylene oxide production at reduced temperature.

Another particular example of an epoxidation process wherein the method of the present invention is applied during operation may proceed as follows. At any time during start-up or operation, when efficiency of the catalyst has decreased to an undesirable level, e.g., a efficiency of about 86% or lower, the operating temperature will be increased to at least about 240° C. and up to about 250° C. for a period of at least about 2 hours, at least about 6 hours, at least about 12 hours, at least about 24 hours, or even about 48 hours. The treatment may be carried out until a desired catalyst efficiency has been reached, or until the catalyst efficiency has increased at least slightly.

During periods at elevated temperatures of 240° C. or above, the feed composition may remain substantially unchanged. Or, oxygen and alkylene concentration may be decreased, e.g., the feed composition may have the oxygen concentration reduced from about 8 mole-% to about 2 mole-%, and may have the alkylene concentration reduced from about 30 mole-% to about 20 mole-%. In such embodiments, carbon dioxide concentration will increase from about 3 mole-% to about 5 mole-% and the overall catalyst chloriding effectiveness value may decrease slightly, e.g., may decrease from about 3 to about 2 when expressed as $Z^*$. If altered during heat treatment, the feed composition may desirably be returned to its original composition when the temperature is reduced.

As those of skill in the art will readily appreciate, other parameters of the epoxidation process may also be adjusted in order to achieve a desired rate of alkylene oxide production during the periods at elevated and/or reduced temperature. For example, the reactor pressure and/or the space velocity may be changed along with or instead of the inlet feed composition in order to achieve a particular production rate at a particular operating temperature.

The alkylene oxide produced by the present epoxidation process may typically be processed to provide further downstream products, such as, for example, 1,2-diols, 1,2-diol ethers, 1,2-carbonates, and alkanolamines. Since the present invention provides an improved epoxidation method, it is contemplated that the improvements provided will carry forward to provide improvements to these downstream processes and/or products. Improved methods for the production of 1,2-diols, 1,2-carbonates, 1,2-diol ethers and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt % sulfuric acid, based on the total reaction mixture, at from about 50° C. to about 70° C. at 1 bar absolute, or in a gas phase reaction, at from about 130° C. to about 240° C. and from about 20 bar to about 40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced via the method of the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The examples presented below are intended to be merely illustrative, and should not be construed to be any sort of limitation on the scope of the claimed invention.

EXAMPLE 1

The present method will be utilized during an operating epoxidation process to enhance the efficiency of the rhenium-promoted catalyst being utilized therein. Relative to the surface area of the support, the silver density of this catalyst is 0.50 g Ag/m$^2$. More particularly, the epoxidation process will be carried out within a CSTR reactor, and the temperature measurements made directly, via thermocouples in the catalyst basket. The design of the CSTR is such that the temperature in the catalyst bed is essentially uniform, i.e., typically within 1° C. At the time of initiation of the method, the epoxidation process will have been operating for 15 days, the temperature will be approximately 230° C. and the catalyst efficiency stable at approximately 86%.

At the end of day 15, the operating temperature will be increased to about 250° C. and held at this value for about two days. The temperature will then be reduced to about 240° C. and held at that temperature for slightly less than one day. Finally, the temperature will be reduced to about 230° C. During the periods at higher temperature, the feed composition will be substantially maintained, i.e., with an inlet oxygen concentration of about 8 mole-%, inlet ethylene concentration of about 30 mole-% and inlet carbon dioxide concentration of about 3 mole-%. The target inlet ethane concentration remains at 0.5 mole-% and the overall catalyst chloriding effectiveness value is initially about 1.3 Z* but is adjusted to about 1.9 Z* after the first day at 250° C. in order to compensate for the gradual decline in activity as the catalyst approaches steady-state operation. The results of this example are shown in FIGS. 1 and 2.

Figure 1:
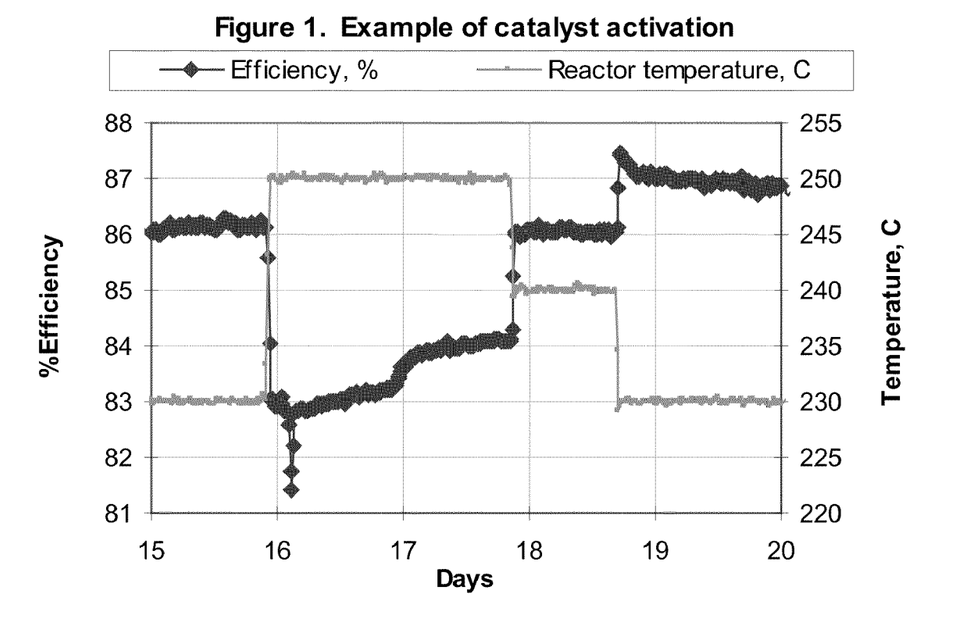
FIG. 1 is a graphical depiction of the % efficiency of an epoxidation catalyst having been subjected to the present method within an epoxidation process.
Figure 2:
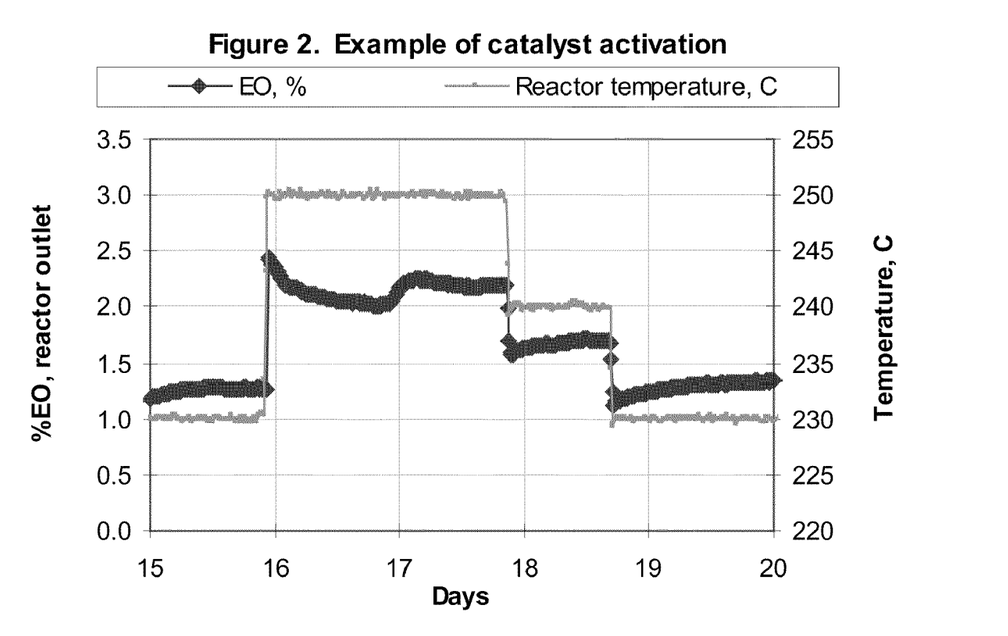
FIG. 2 is a graphical depiction of the ethylene oxide production rate of an epoxidation process before, during and after the catalyst utilized therein is subjected to the present method.

In summary, and as is shown in FIG. 1, after returning to an operating temperature of 230° C., the catalyst efficiency will have increased to about 87 percent, an improvement of about one percentage point. During the periods of efficiency enhancement/activation at elevated temperature of 250° C. and 240° C., the catalyst will remain in operation, producing ethylene oxide (EO). As shown in FIG. 1, the efficiency drops during the period at 250° C., but then returns to about the original value at 240° C. As shown in FIG. 2, the EO production rate will increase above the original value during the activation periods but surprisingly, will return essentially to the original value when the temperature is reduced to 230° C. That is, there will be substantially no loss of production during the activation periods.

EXAMPLE 2 AND COMPARATIVE EXAMPLE 3

These examples illustrate the effect of operating a catalyst during initial startup according to one embodiment of the present method, at temperatures of 240° C. or greater before reducing the temperature to 230° C. or lower.

Two unused 40-cc samples of the same Re-promoted silver catalyst batch as used in Example 1 are charged to CSTR reactors as used in Example 1 and started up using the following reaction conditions: target inlet feed composition of 8 mole-% oxygen, 30 mole-% ethylene, 3 mole-% carbon dioxide, 0.5 mole-% ethane, 2 ppmv ethyl chloride; reactor pressure 2000 kPa absolute (275 psig); total flow 320 standard liters per hour (11.3 scfh), measured as nitrogen.

Figure 3:
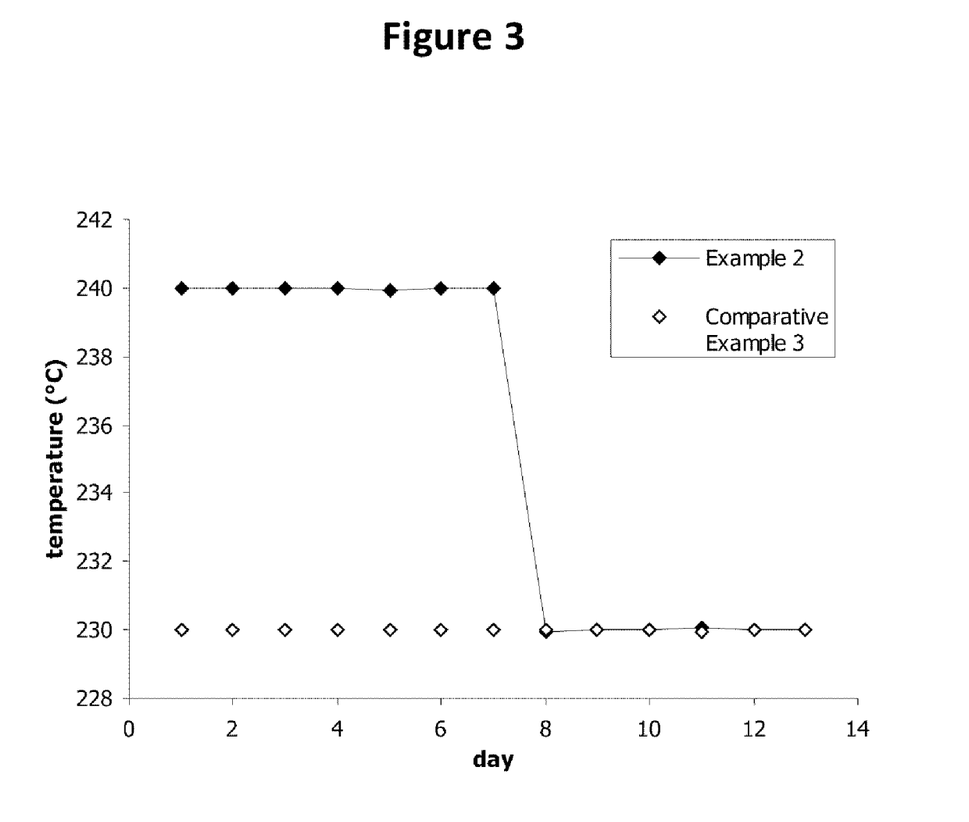
FIG. 3 is a graphical depiction of the temperature profile utilized in an Example conducted according to one embodiment of the present method and a comparative Example conducted according to a conventional method.
Figure 4:
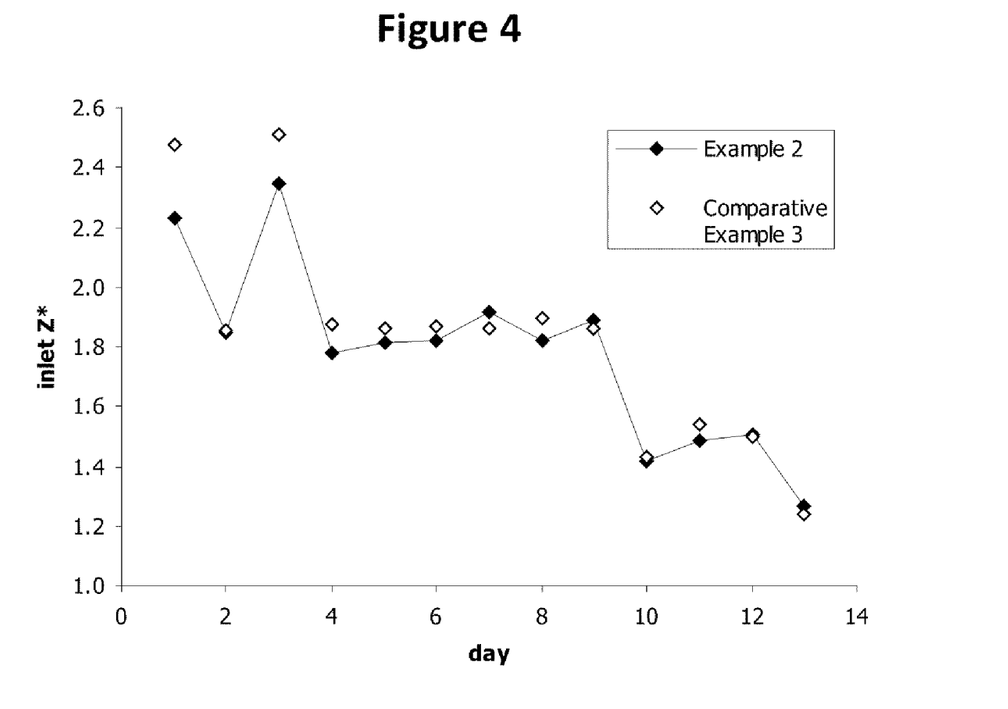
FIG. 4 is a graphical depiction of the inlet Z* profile for an Example conducted according to one embodiment of the present method and a comparative Example conducted according to a conventional method.

For Example 2, the reactor temperature is set at 240° C. while for Comparative Example 3, the reactor temperature is set at 230° C. The temperature profile for each example is shown in FIG. 3. As shown in the Figure, these temperatures are maintained for the first seven days of each run. Over this period, the target inlet ethyl chloride concentrations are varied in parallel in order to determine the catalyst responses to inlet overall catalyst chloriding effectiveness value (Z*). The inlet overall catalyst chloriding effectiveness value (Z*) profile for each example is shown in FIG. 4.

Through Day 7, the cumulative productions are 0.035 and 0.031 kT EO per cubic meter of catalyst (2.2 and 1.9 Mlb EO per cubic foot catalyst) for the runs of Example 2 and Comparative Example 3, respectively.

For Day 8, the reactor temperature for the run of Example 2 is decreased from 240° C. to 230° C. As shown below in Table 1, between Days 9 and 13, the two reactors are operated under essentially identical conditions as the target inlet ethyl chloride concentrations are again varied in parallel to examine the Z* responses. While the resulting catalyst productivity as measured by the concentration of ethylene oxide in the reactor outlet stream is slightly lower for the run of Example 2, the corresponding efficiency is more than one percentage point better than that of the run of Comparative Example 3 on the same day. These examples thus show that application of one embodiment of the present method, even during a start-up period, can provide an increased catalyst efficiency relative to conventional methods.

TABLE 1

| | Example 2 | | | | Comparative Example 3 | | | |
|---|---|---|---|---|---|---|---|---|
| day | T (° C.) | Z* | % EO | % eff | T (° C.) | Z* | % EO | % eff |
| 9 | 230 | 1.89 | 1.42 | 87.1 | 230 | 1.86 | 1.56 | 85.3 |
| 10 | 230 | 1.42 | 1.35 | 87.2 | 230 | 1.43 | 1.48 | 85.7 |
| 11 | 230 | 1.48 | 1.36 | 87.0 | 230 | 1.54 | 1.48 | 85.5 |
| 12 | 230 | 1.51 | 1.39 | 86.9 | 230 | 1.50 | 1.48 | 85.5 |
| 13 | 230 | 1.27 | 1.31 | 86.9 | 230 | 1.24 | 1.40 | 85.7 |

While only certain features of the invention have been illustrated and described herein, many modifications and changes will occur to those skilled in the art. The examples above further illustrate the invention, without limiting the scope thereof. It is to be understood that the appended claims are intended to cover all such modifications and changes as fall within the true spirit of the invention.

We claim:

1. A method for enhancing the efficiency of a rhenium-promoted epoxidation catalyst in situ comprising contacting the catalyst with a feed comprising a gas phase epoxidation reaction promoter at an elevated temperature of from at least about 240° C. to less than or equal to about 250° C. for at least about 2 hours and then reducing the temperature to a reduced temperature of less than or equal to about 230° C., wherein the feed further comprises carbon dioxide at a concentration of at most 5 mole % when the temperature is at least about 240° C.

2. The method of claim 1, wherein the epoxidation catalyst further comprises one or more additional promoters comprising lithium, sodium, potassium, rubidium, cesium, beryllium, magnesium, calcium, strontium, barium, nitrogen, sulfur, manganese, tantalum, molybdenum and tungsten.

3. The method of claim 2, wherein the one or more additional promoters comprise(s) cesium.

4. The method of claim 1, wherein the gas phase epoxidation reaction promoter comprises an organic halide.

5. The method of claim 4, wherein the organic halide comprises chloride.

6. The method of claim 5, wherein the organic halide is methyl chloride, ethyl chloride, ethylene dichloride, vinyl chloride, or any combination of two or more of these.

7. The method of claim 1, wherein the feed further comprises oxygen, ethylene, carbon dioxide, water, or any combination of these.

8. The method of claim 1, wherein the efficiency of the epoxidation catalyst is increased by at least about 0.5%.

9. The method of claim 8, wherein the efficiency of the epoxidation catalyst is increased by at least about 1.0%.

10. The method of claim 1, wherein the gas phase promoter concentration in the feed remains the same at the elevated and reduced temperatures.

11. The method of claim 10, wherein the gas phase promoter concentration in the feed is caused to differ at the elevated and reduced temperatures.

12. A method for the epoxidation of one or more alkylenes comprising contacting a rhenium-promoted epoxidation catalyst with a feed comprising a gas phase epoxidation reaction promoter, oxygen and one or more alkylenes at an elevated temperature of from at least about 240° C. to less than or equal to about 250° C. for at least about 2 hours, and subsequently reducing the temperature to a reduced temperature of less than or equal to about 230° C., wherein the feed further comprises carbon dioxide at a concentration of at most 5 mole % when the temperature is at least about 240° C.

13. The method of claim 12, wherein the feed further comprises carbon dioxide.

14. The method of claim 12, wherein the alkylene comprises ethylene.

15. The method of claim 12, wherein the concentration of the gas phase promoter, oxygen and one or more alkylenes remains the same at the elevated and reduced temperatures.

16. The method of claim 12, wherein the concentration of at least one of the gas phase promoter, oxygen and/or one or more alkylenes is caused to differ at the elevated and reduced temperatures.

17. The method of claim 16, wherein the concentration of at least two of the gas phase promoter, oxygen and/or one or more alkylenes is caused to differ at the elevated and reduced temperatures.

18. A method for making a 1,2-diol, a 1,2-diol ether, a 1,2-carbonate, or an alkanolamine comprising converting an alkylene oxide into the 1,2-diol, a 1,2-diol ether, a 1,2-carbonate, or alkanolamine, wherein the alkylene oxide has been prepared by a method for the epoxidation of alkylenes comprising contacting a rhenium-promoted epoxidation catalyst with a feed comprising a gas phase epoxidation reaction promoter, oxygen and one or more alkylenes at an elevated temperature of from at least about 240° C. to less than or equal to about 250° C. for at least about 2 hours, and subsequently reducing the temperature to a reduced temperature of less than or equal to about 230° C., wherein the feed further comprises carbon dioxide at a concentration of at most 5 mole % when the temperature is at least about 240° C.

* * * * *